(12) United States Patent
McCraw

(10) Patent No.: US 10,470,696 B1
(45) Date of Patent: Nov. 12, 2019

(54) METHOD FOR ASSESSING INTERPERSONAL RAPPORT AND COMPATIBILITY USING BRAIN WAVES

(71) Applicant: John McCraw, Anaheim, CA (US)

(72) Inventor: John McCraw, Anaheim, CA (US)

(*) Notice: Subject to any disclaimer, the term of this patent is extended or adjusted under 35 U.S.C. 154(b) by 470 days.

(21) Appl. No.: 15/183,617

(22) Filed: Jun. 15, 2016

Related U.S. Application Data

(60) Provisional application No. 62/180,621, filed on Jun. 17, 2015.

(51) Int. Cl.
*A61B 5/04* (2006.01)
*A61B 5/16* (2006.01)
*A61B 5/0482* (2006.01)

(52) U.S. Cl.
CPC .......... *A61B 5/167* (2013.01); *A61B 5/04012* (2013.01); *A61B 5/0482* (2013.01)

(58) Field of Classification Search
None
See application file for complete search history.

(56) References Cited

U.S. PATENT DOCUMENTS

| | | | | |
|---|---|---|---|---|
| 7,676,466 B2* | 3/2010 | Terrill | ........ | G06Q 50/01 707/999.006 |
| 8,989,835 B2* | 3/2015 | Badower | ........ | A61B 5/00 600/383 |
| 2005/0154603 A1* | 7/2005 | Adams | ........ | G06Q 30/02 705/319 |
| 2005/0177058 A1* | 8/2005 | Sobell | ........ | A61B 5/0484 600/545 |
| 2007/0031800 A1* | 2/2007 | Solomon | ........ | G06Q 30/02 434/322 |
| 2013/0131755 A1* | 5/2013 | Panken | ........ | A61B 5/7475 607/45 |
| 2015/0199010 A1* | 7/2015 | Coleman | ........ | A61B 5/0006 345/156 |
| 2016/0038049 A1* | 2/2016 | Geva | ........ | A61B 5/048 600/544 |
| 2016/0113545 A1* | 4/2016 | Kim | ........ | A61B 5/04842 600/544 |
| 2017/0216595 A1* | 8/2017 | Geva | ........ | A61N 1/36025 |
| 2017/0228512 A1* | 8/2017 | Driscoll | ........ | G06F 19/3418 |

* cited by examiner

*Primary Examiner* — Sunit Pandya

(57) ABSTRACT

An improved method for assessing rapport and potential compatibility between two or more persons, including collecting a sample profile of the brain wave patterns of each person, analyzing the profiles and comparing the characteristics of each profile with the profile or profiles of other individuals according to predetermined criteria.

3 Claims, 3 Drawing Sheets

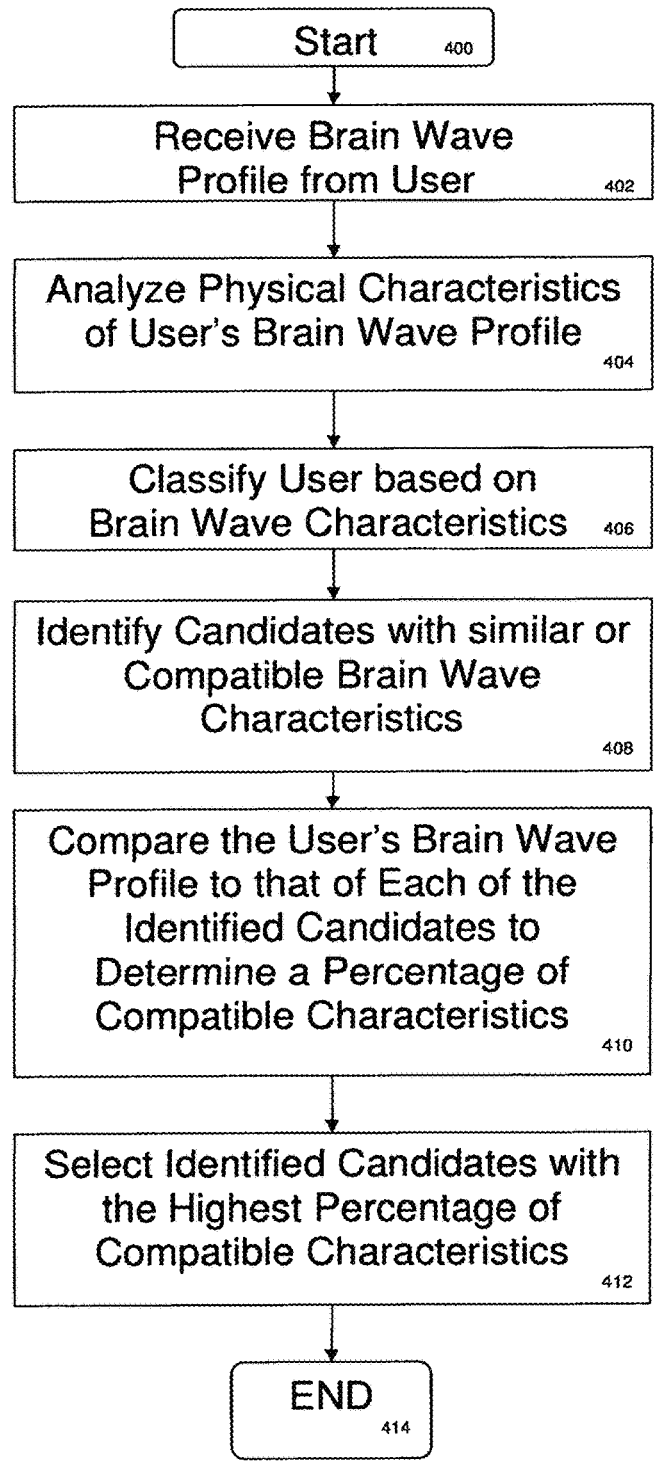

US 10,470,696 B1

METHOD FOR ASSESSING INTERPERSONAL RAPPORT AND COMPATIBILITY USING BRAIN WAVES

CROSS-REFERENCE TO RELATED PATENT APPLICATION

This Application claims the benefit of PPA Ser. No. 62/180,621 Filed Jun. 17, 2015 by John McCraw which is incorporated herein by reference.

FEDERALLY SPONSORED RESEARCH

N/A

SEQUENCE LISTING

N/A

FIELD

This relates to a method for assessing rapport and potential compatibility between individuals based upon brain wave patterns.

BACKGROUND & DESCRIPTION OF RELATED ART

Historically there have been numerous attempts to understand the complicated interpersonal dynamics that occur between people, including why people often appear to be more compatible with some people than they do with others.

To this day the phenomenon is little understood and only vaguely referred to as "Chemistry" between people.

As a result, actual chemical explanations have been sought and developed in an attempt to artificially enhance attraction and rapport between individuals, as in the case of "Pheromones" (e.g. U.S. Pat. No. 5,278,141 A (Berliner 1993) and references therein).

Many cultures believe that the reason some people seem to have an instant rapport while others take an instant, irrational dislike to each other can be attributed to Karmic "Past Life" Experiences. Various techniques have been developed to recover those "hidden memories" (e.g. US 20060188857 A1 (Knowles 2005) and references therein).

While there are countless areas in which human rapport and compatibility is essential—from corporate project teams, athletic sports teams, military units and law enforcement partners to onstage chemistry between actors—rapport and compatibility assessment is currently used most prominently in romantic dating or "matchmaking" services.

A "matchmaking service" attempts to identify and unite two or more people presumed to be candidates for a compatible relationship.

From the earliest days of "matchmaking", there have been attempts to analyze, assess and predict compatibility between individuals. The Astrological "Compatibility Chart", for example, has existed for centuries and has even been updated for the computer age (e.g. US 20020160338 A1 (Yirmeyahu 2001) and references therein). However, due to a lack of scientific evidence in support, Astrology today lacks scientific credibility.

WO 2013003916 A1 (Penna 2013) describes a modern day, computerized bracelet that calculates "compatibility" based on the ancient, but unscientific, criteria of Numerology.

Current "matchmaking" services focus primarily on criteria such as various psychological and "personality traits" as determined by survey questionnaires (e.g. U.S. Pat. No. 8,635,167 B2 (Buckwalter et al. 2014) and references therein).

However, such methods are limited by the fact that they are subjective and subject to the pitfalls of "self-reporting". People can, and frequently do, deliberately or unintentionally misrepresent themselves or even lie outright.

Other "matchmaking" approaches focus solely on physical characteristics such as facial features, (e.g. U.S. Pat. No. 7,055,103 B2 (Itzhak Lif 2001) and references therein). This superficial approach makes no attempt to address the deeper elements of personal rapport or long-term compatibility.

Consequently there is a recognized need for, and it would be desirable to have, a method for assessing rapport and potential compatibility between individuals based upon purely objective (non-subjective) criteria consistent with longstanding, proven scientific principles.

For nearly 100 years, the Electroencephalograph (EEG) has been used as a tool in the medical field to map and record the electrical brain wave activity of patients and to assist physicians in diagnosing and treating various brain disorders such as epilepsy, strokes, Alzheimer's diseases etc.

EEGs have also been used as an aid in biofeedback training, (e.g. U.S. Pat. No. 6,097,981 A (Freer 1997) and references therein) in which electrical brain wave activity is visually and/or audibly displayed in real time allowing subjects to monitor and regulate the activity.

More recently consumer grade EEGs have been used for entertainment purposes such as in video gaming systems, (e.g. US 20100240458 A1 (Gaiba, Squarise & Godina 2010) and references therein and U.S. Pat. No. 5,213,338 A (Brotz 1991) and references therein).

EEG technology has also been developed for use as a "Lie Detector" (e.g. U.S. Pat. No. 5,406,956 (Farwell 1993) and references therein).

US 20050177058 A1 (Sobell 2005) describes a limited method "by means of which the compatibility (habit, hobby, personality and etc.) of more than one subject can be studied using their EEG readings when a common set of stimuli are presented to them." Such a method requires the use of common outside stimuli and narrowly defines "compatibility" in terms of "habit, hobby, personality and etc."

In fact, such an approach doesn't measure "compatibility" so much as a mutual interest (or disinterest) in the particular stimuli being presented. Furthermore, outside stimuli will increase Beta Wave activity, interfering with other "natural state" waves.

US 20110015536 A1 (Milgramm 2009) describes a method for using EEG data to determine potential compatibility with a workplace environment but not with potential co-workers.

SUMMARY & ADVANTAGES

The following presents a simplified summary in order to provide a basic understanding of some aspects of the method. The summary is not an extensive overview of the method. It is neither intended to identify key or critical elements nor to delineate the scope of the method. The following summary merely presents some concepts in a simplified form as a prelude to the description below.

The present method is for a brain wave-based assessment of rapport and potential compatibility between two or more persons, the method including, but not limited to, (a) collecting an EEG sample of each person's brain wave output;

(b) analyzing the EEG sample to define specific characteristics; (c) comparing the EEG brain wave sample to EEG brain wave samples similarly collected from one or more other persons according to pre-determined criteria; and (d) storing the samples for comparison to the similarly collected brain wave samples of other persons.

Brain waves, like sound waves and light waves, function according to the exact same scientific principles and laws of physics that govern all waves, including the way that they interact in the presence of other, similar waves. Two or more wave patterns, for example, can be demonstrated to be "in sync" or "out of sync" in relation to each other.

Sound waves "in sync" resonate to produce harmonious sounds. "Out of sync" sound waves produce dissonance. Light waves, as represented by the color spectrum, either blend ("in sync") or clash ("out of sync").

Similarly, Brain Waves, to varying degrees, will either blend harmoniously "in sync" or clash in dissonance if "out of sync".

Brain wave analysis and comparison fills a need for an objective, scientifically-based method for assessing rapport and potential compatibility between individuals by comparing wave characteristics including, but not limited to, Wavelengths, Amplitude, Frequency and Speed, to determine, among other factors, whether their brain waves are "in sync" or "out of sync".

The method is not intended to be limited solely to EEG output but may also be developed with other physiological wave data including, but not limited to EKG, Heart-rate, ECG and/or any combination thereof.

Advantages

The advantages of a Brain Wave based assessment of potential rapport and compatibility between two or more persons over other systems of prior art include the following:

1. SCIENTIFICALLY BASED—Unlike the prior art based on Astrology, Past Life Regression, Numerology and other methods that lack scientific credibility, the well-established science of physics governs how all waves, including brain waves, interact "in sync" or "out of sync" in the presence of other waves in accordance with proven, long-standing scientific principles.

2. OBJECTIVE—Unlike prior art based on subjective criteria, such as self-reported surveys, questionnaires, personality tests etc., a Brain Wave based assessment is completely objective. Brain waves don't lie.

3. SELF-CONTAINED—Unlike the brain wave based method described in WO 2013003916 A1, which requires people to react to common outside stimuli for comparison, thus increasing Beta Wave activity, the present method is preferable and more accurate in that it compares subject brain waves in their natural state without the need for, or interference by, outside stimuli.

4. NATURAL—Furthermore, WO 2013003916 A1 limits "compatibility" in terms of "habits, hobbies, personalities etc." unlike the present method which focuses exclusively and objectively on the natural-state brain waves themselves, independent of any such external and extraneous factors.

5. MULTIPLE USES—Finally, the present method provides for storage of EEG profiles in a database against which a subject profile can be matched against multiple profiles for a variety of purposes.

The present method fulfills a recognized need for a method of assessing rapport and potential compatibility between individuals based upon objective, non-subjective criteria consistent with long-standing, proven scientific principles that is both novel and unobvious from the prior art.

BRIEF DESCRIPTION OF THE DRAWINGS

FIG. 4 illustrates the process embodied as a method for using empirical data prepared from Brain Wave analysis to match an individual with one or more other candidates.

DETAILED DESCRIPTION

Figure 1:
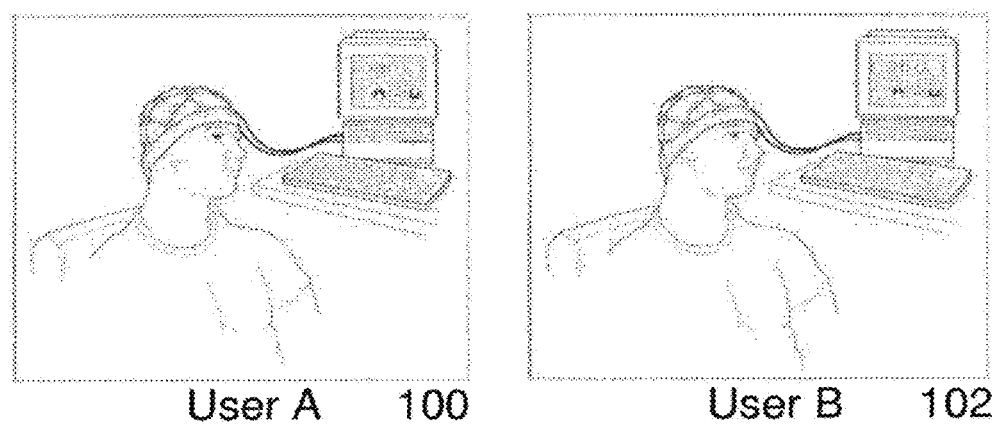
FIG. 1 illustrates two individuals using Electroencephalograph (EEG) hardware and software on a computer to record Brain Wave activity

The principles and operation of the improved method for assessing rapport and potential compatibility according to the present method may be better understood with reference to the accompanying description.

Before explaining at least one embodiment of the process in detail, it is to be understood that the process is not limited in its application to the details set forth in the following description or illustrated in any images. The process is capable of other embodiments and ramifications and of being practiced or carried out in various ways. Also, it is to be understood that the phraseology and terminology employed herein is for the purpose of description and should not be regarded as limiting.

In the described method, there are various ways of obtaining and comparing the Brain Wave characteristics of two or more persons.

1. In one embodiment, two or more subjects (persons) each use EEG hardware (FIGS. 1, 100 & 102) to read and display sample profiles of their brain wave patterns. These sample profiles are then analyzed and compared according to pre-determined criteria, including, but not limited to, similarities and differences in the physical characteristics of the waves (FIG. 2) including, but not limited to, wavelengths, frequency, amplitude, speed and Harmonic Resonance, individually and in comparison to each other (FIG. 2), to determine the degree to which the brain waves Resonate or are "in sync" or "out of sync" with each other (FIG. 3).

2. A second embodiment is similar to #1 above except that the output analysis, comparison and assessment are automated with dedicated software, either at the same location or across a network (such as the Internet).

3. In another embodiment, individual brain wave profiles are collected as in #1 above and stored in a database. A subject uses EEG hardware to read and display a brain wave pattern which is then analyzed and compared as in #1 above, manually by trained analysts or automatically with dedicated software, to other subject profiles contained within the database for rapport and/or compatibility assessment between subjects (FIG. 4).

4. In one ramification, "Matchmaking" or "Dating" businesses may use the methods described above to match clients according to similarities in their brain wave activity.

5. In another ramification, Individuals may use a handheld processor and mobile application to analyze, compare and contrast the Brain Wave Profiles of others with that of the Individual user for degrees of similarities, differences and resonance to evaluate potential rapport & compatibility between the individuals.

6. In another ramification, "home kits", consisting of EEG hardware and/or all necessary software, may be sold or distributed to individuals, along with all training materials necessary for home use.

7. In another ramification, organizational "team leaders", including but not limited to, for example, corporate or athletic team leaders, may use the method above to assess the potential compatibility of potential new "team recruits" with preexisting team members.

8. In another ramification, Law Enforcement Interrogation techniques may be enhanced by matching interrogators with subjects according to potential rapport as determined by brain wave activity.

9. In another ramification, Jury Selection in Court cases may be enhanced by using the method to select potentially compatible jurors.

These are a just a few examples of the potential embodiments and ramifications. Many other embodiments and ramifications are possible and the above examples should not be construed as limiting in any way. The process can ultimately be applied to enhance any human endeavor that requires rapport, communication and cooperation between two or more individuals.

Operation:

All of the above embodiments and ramifications follow the same basic format:

Two or more subjects (persons) use an Electroencephalograph (FIGS. 1, 100 & 102) to produce individual brain wave sample profiles which are then analyzed, compared (FIG. 2) and assessed, either manually or automatically, visually or audibly, manually or using dedicated software, according to pre-determined criteria, for potential compatibility with each other (FIG. 3) or with one or more other brain wave sample profiles recorded and stored in a database (FIG. 4).

FIG. 3 illustrates an embodiment of a method for assessing potential compatibility between two or more Individuals. The method begins at Start Block 300.

At Process Block 302, Empirical Data, in the form of Brain Wave Profiles, are collected from two or more Individuals through EEG Hardware and Software as illustrated in FIG. 1.

At Process Block 304, the empirical data from each individual, in the form of Brain Wave Profiles, are analyzed as to their unique physical characteristics including, but not limited to, wavelength, frequency, amplitude and speed.

At Process Block 306, the Individuals are classified into categories according to the physical characteristics of their Profiles as analyzed above.

Figure 2:
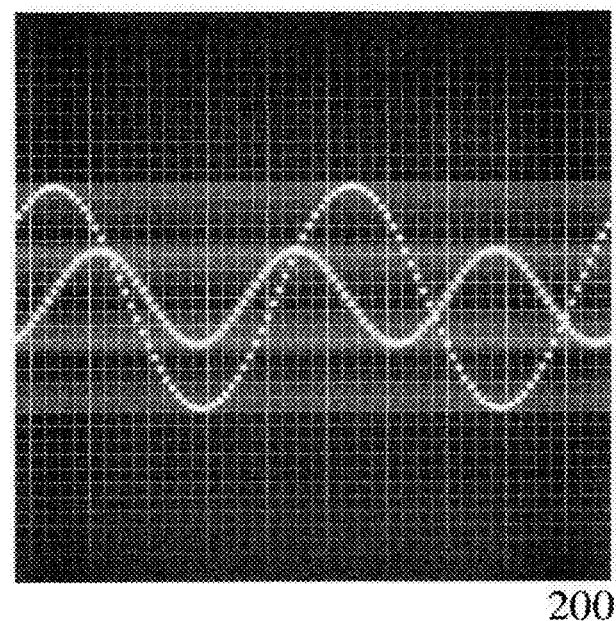
FIG. 2 illustrates a comparison of two different waves.
Figure 3:
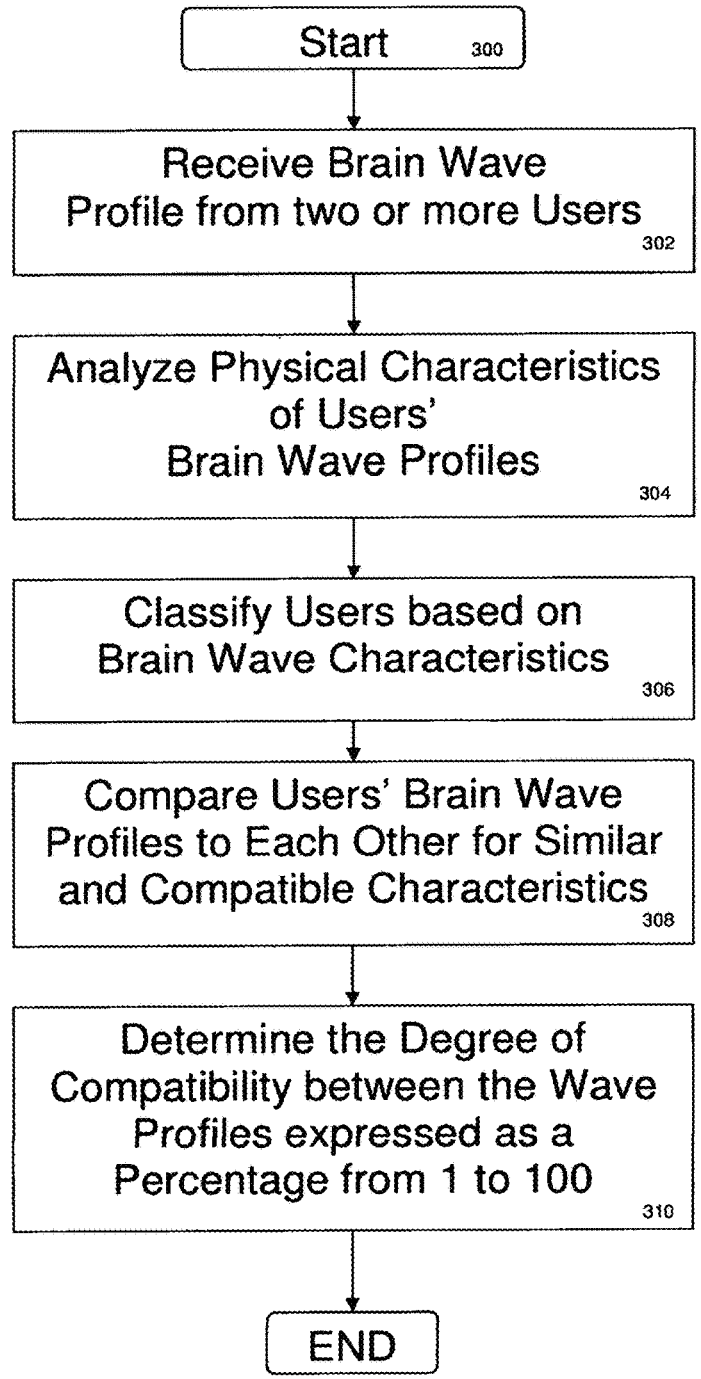
FIG. 3 illustrates the process embodied as a method for using empirical data prepared from Brain Wave analysis to assess potential rapport and compatibility between Individuals.

At Process Block 308, the Brain Wave Profiles of the Individuals are compared to each other according to pre-determined criteria, including, but not limited to, similarities and differences in the physical characteristics of the waves as illustrated in FIG. 2 (200) and including, but not limited to, wavelengths, frequency, amplitude, speed and Harmonic Resonance, to determine the degree to which the brain waves Resonate or are "in sync" or "out of sync" with each other.

At Process Block 310, the degree of compatibility between the Brain Wave Profiles is determined and expressed as a percentage from 1 to 100%.

The Method terminates at End Block 312.

FIG. 4 illustrates an embodiment of the method for matching a User with one or more potentially compatible candidates. The method begins at Start Block 400.

At Process Block 402, Empirical Data in the form of Brain Wave Profiles are collected from two or more Individuals through EEG Hardware and Software as illustrated in FIG. 1.

At Process Block 404 the empirical data from each individual, in the from of Brain Wave Profiles, are analyzed as to their unique physical characteristics including, but not limited to, wavelength, frequency, amplitude and speed.

At Process Block 406, the Individuals are classified into categories according to the physical characteristics of their Profiles as analyzed above.

At Process Block, 408 potentially compatible candidates are identified according to pre-determined criteria including, but not limited to, similarities and differences in the physical characteristics of the waves as illustrated in FIG. 2 and including, but not limited to, wavelengths, frequencies, amplitude, speed and Harmonic Resonance.

At Process Block 410, a User's Brain Wave Profile is compared to the profiles of all potentially compatible candidates identified above to determine a percentage of compatible characteristics.

At Process Block 412 the Candidates with the highest percentage of compatible characteristics are selected.

The Method Terminates at End Block, 414.

Other embodiments, combinations and modifications of this method may readily occur to those of ordinary skill in the art. Therefore, this process is to be limited only by the following claims which include all such embodiments and modifications when viewed in conjunction with the above specifications and accompanying drawings.

PATENT CITATIONS

U.S. Pat. No. 5,278,141 A Fragrance compositions containing human pheromones
  David L. Berliner Filed: Mar. 8, 1993 Published: Jan. 11, 1994
US 20060188857 A1 Self-awareness training method and apparatus
  John Knowles Filed: Feb. 18, 2005 Published: Aug. 24, 2006
US 20020160338 A1 Compatibility Calculator and Matchmaking by Horoscope
  Vladimir Yirmeyahu Filed: Feb. 16, 2001 Published: Oct. 31, 2002
WO 2013003916 A1 Bracelet indicating compatibility between persons through numerological synastry
  Maria Penna Filed: Jul. 12, 2011 Published: Jan. 10, 2013
U.S. Pat. No. 8,635,167 B2 Method & System for Identifying People Who Are Likely To Have a Successful Relationship
  J. Galen Buckwalter Filed: Oct. 10, 2008 Published: Apr. 23, 2009
U.S. Pat. No. 7,552,060 B2 Method for determining compatibility
  Herb D. Vest Filed: Aug. 11, 2005 Published: Jun. 23, 2009
U.S. Pat. No. 7,055,103 B2 Method of matchmaking service
  Itzhak Lif Filed: Aug. 28, 2001 Published: May 30, 2006
U.S. Pat. No. 6,097,981 A Electroencephalograph based biofeedback system & method
  Peter A. Freer Filed: Dec. 2, 1997 Published: Aug. 1, 2000
US 20100240458 A1 Video game hardware systems and software methods using electroencephalography Andrea Gaiba Filed: Mar. 22, 2010 Published: Sep. 23, 2010

U.S. Pat. No. 5,213,338 A Brain wave-directed amusement device

Gregory R. Brotz Filed: Sep. 30, 1991 Published: May 25, 1993

U.S. Pat. No. 5,406,956 Method and apparatus for truth detection

Lawrence A. Farwell Filed: Feb. 11, 1993 Published: Apr. 18, 1995

US 20050177058 A1 System and method for analyzing the brain wave patterns of one or more persons for determining similarities in response to a common set of stimuli, making artistic expressions and diagnosis Nina Sobell Filed: Feb. 10, 2005 Published: Aug. 11, 2005

US 20110015536 A1 EEG-based method for determining a subject's compatibility with a work environment Michael Milgramm Filed: Jul. 17, 2009 Published: Jan. 20, 2011

What is claimed:

1. A method of assessing rapport and potential compatibility among two or more individuals comprising:
   a. Using a processor and Electroencephalographic (EEG) hardware and software designed to read, record and display visually and audibly, at least one electrical signal associated with the brain activity of the user to obtain a sample of the Brain Wave pattern of each individual without reference to the presence or absence of any particular external stimuli;
   b. Using the processor to analyze the properties and characteristics of said sample of the Brain Wave pattern, and to generate a unique Brain Wave Profile of each individual based upon properties and characteristics, including visual and audible signals associated with the brain activity;
   c. Using the processor to classify each individual based on the properties and characteristics of said Brain Wave Profile;
   d. Using a processor to analyze, compare and contrast said Brain Wave Profiles with each other for degrees of similarities, differences and resonance to determine potential rapport and compatibility between the individuals; and
   e. Using a Database to store said Brain Wave Profiles for future analyses and comparisons with the Brain Wave Profiles of other individuals.

2. The method of claim 1 further comprising:
   a. Using a processor to identify a plurality of candidates from said database for potential rapport and compatibility with an individual and;
   b. Generating a rapport index for the individual and each particular candidate.

3. The method of claim 1 further comprising:
   a. Using a mobile application and handheld processor to transmit the Individual's Brain Wave Profile and;
   b. Using a mobile application and handheld processor to receive the similarly transmitted Brain Wave Profiles of others within a user-defined radius and;
   c. Using a handheld processor and mobile application to analyze, compare and contrast said Brain Wave Profiles of others with that of the Individual user for degrees of similarities, differences and resonance to determine potential rapport and compatibility between the individuals and;
   d. Using a handheld processor and mobile application to emit a signal to alert the Individual when said Brain Wave Profiles of others are determined to have a high potential for rapport and compatibility with the Individual.

* * * * *